United States Patent
Morgenthaler et al.

(10) Patent No.: US 11,760,957 B2
(45) Date of Patent: Sep. 19, 2023

(54) COMPOSITIONS CONTAINING FENCHOLS AND METHODS OF USE

(71) Applicant: BEDOUKIAN RESEARCH, INC., Danbury, CT (US)

(72) Inventors: Dominic S. Morgenthaler, West Caldwell, NJ (US); Veronica M. McBurnie, Leonardo, NJ (US)

(73) Assignee: BEDOUKIAN RESEARCH INC., Danbury, CT (US)

( * ) Notice: Subject to any disclaimer, the term of this patent is extended or adjusted under 35 U.S.C. 154(b) by 0 days.

(21) Appl. No.: 17/091,071

(22) Filed: Nov. 6, 2020

(65) Prior Publication Data
US 2021/0139811 A1 May 13, 2021

Related U.S. Application Data

(60) Provisional application No. 62/932,951, filed on Nov. 8, 2019.

(51) Int. Cl.
C11B 9/00 (2006.01)
A23L 27/20 (2016.01)
A23L 29/00 (2016.01)
A61K 8/34 (2006.01)

(52) U.S. Cl.
CPC .......... *C11B 9/0049* (2013.01); *A23L 27/203* (2016.08); *A23L 29/035* (2016.08); *A61K 8/34* (2013.01)

(58) Field of Classification Search
CPC .................................................... C11B 9/0049
See application file for complete search history.

(56) References Cited

U.S. PATENT DOCUMENTS

2011/0045069 A1   2/2011   Ley et al.
2013/0071544 A1   3/2013   Alexander
2019/0046426 A1*  2/2019   Coulston ................. A61L 9/014

FOREIGN PATENT DOCUMENTS

WO   2019110630 A1   6/2019

OTHER PUBLICATIONS

The Good Scents Company. 2-ethyl fenchol https://web.archive.org/web/20060605023622/http://www.thegoodscentscompany.com/data/rw1024171.html (Year: 2006).*

(Continued)

*Primary Examiner* — Arrie L Reuther
(74) *Attorney, Agent, or Firm* — Ohlandt, Greeley and Perle, LLP

(57) ABSTRACT

This disclosure provides a composition containing: (i) at least one material having odor strength or olfactive character; and (ii) at least one fenchol. The at least one fenchol is selected from an alkylated fenchol, an isomeric, diastereomeric or enantiomeric alkylated fenchol, or mixtures thereof. The at least one fenchol is present in an amount effective to enhance odor strength or olfactive character of the composition. The composition can be a synergistic composition. This disclosure also provides a method of enhancing odor strength or olfactive character of a composition by adding at least one fenchol to at least one material having odor strength or olfactive character in an amount effective to enhance odor strength or olfactive character of the composition.

14 Claims, 10 Drawing Sheets

|  | w/o | w/ Ethyl Fenchol (1 ppm unless otherwise specified) | Total Panelists |
|---|---|---|---|
| **Cardamom Oil (*5 ppm)** | 1 | 6 | 7 |
| Cinnamon Leaf Oil | 1 | 6 | 7 |
| Clove Leaf Oil | 1 | 6 | 7 |
| Nutmeg Oil | 1 | 6 | 7 |
| Elemi Oil | 1 | 6 | 7 |
| Rosemary Oil | 2 | 5 | 7 |
| Sandalwood Oil Australian | 2 | 5 | 7 |
| Rose Oil Bulgarian | 2 | 5 | 7 |
| Patchouli Oil | 0 | 6 | 6 |
| Clearwood Oil | 1 | 6 | 7 |
| Cashmeran | 1 | 6 | 7 |
| Lemon Oil | 2 | 5 | 7 |
| Ginger Oil | 2 | 5 | 7 |
| Methyl Ionone 95% | 0 | 5 | 5 |
| Methyl Ionone 70% | 1 | 6 | 7 |

(56) References Cited

OTHER PUBLICATIONS

Fenchol Chemical Structure ChemSpider.com/Chemical-Structure. 5365080.html obtained Oct. 29, 2021 (Year: 2021).*
Basenotes "I wanna be a mushroom. And may be something bigger . . . " Oct. 16, 2019 (Oct. 16, 2019) <https://www.basenotes.net/threads/470379-I-wanna-be-mushroom-And-may-be-something-bigger>: p. 1, para 1, 8.
Badgerandblade "Aroma chemicals in shaving products, scent profiles and allergies" Sep. 17, 2019 (Sep. 17, 2019) <https://www.badgerandblade.com/forum/threads/aroma- chemicals-in-shaving-products-scent-profiles-and-allergies.573830/>; p. 1, para 1, p. 2, para 7.
International Written Opinion for corresponding international application PCT/US 20/59307, 7 pages, dated Feb. 3, 2021.
International Search Report and Written Opinion for corresponding international application PCT/US 20/59307, 7 pages, dated Feb. 3, 2021.
Gosselin et al "Synthesis of Earthy-Mouldy Smelling Compounds-11Ethyl α and β-Fenchols" Tetrahedron Letters, 1990, vol. 31, No. 22, pp. 3151-3154, Pergamon Press plc, Oxford UK.
Finato et al "Synthesis of New Earthy Odorants", J. Agric. Food Chem. 1992, 40, 857-859, American Chemical Society, Washington, DC, US.
International Preliminary Report on Patentability for corresponding international application PCT/US 20/59307, 109 pages, dated Oct. 7, 2021.

\* cited by examiner

Fig. 1

|  | Without | W/ Terrasol | W/ Methyl Fenchol | W/ Fenchol | Total Panelists |
|---|---|---|---|---|---|
| Rosemary EO | 1 | 1 | 3 | 1 | 6 |
| Nutmeg EO | 0 | 4 | 1 | 1 | 6 |
| Clearwood Bio Based | 1 | 5 | n/a | n/a | 6 |
| Patchouli EO | 1 | 2 | 3 | 0 | 6 |
| Natural/Synthetic Mix | 0 | 5 | 0 | 0 | 5 |
|  |  |  |  |  |  |

Fig. 2

|  | Without | W/ Methyl Fenchol | Total Panelists |
|---|---|---|---|
| Spice Market | 0 | 6 | 6 |

|  | Without | W/ Fenchol | Total Panelists |
|---|---|---|---|
| Spice Market | 1 | 5 | 6 |

|  | Without | W/ Propyl Fenchol | Total Panelists |
|---|---|---|---|
| Spice Market | 1 | 5 | 6 |

|  | Without | W/ Butyl Fenchol | Total Panelists |
|---|---|---|---|
| Spice Market | 1 | 5 | 6 |

|  | Without | W/ t-Butyl Fenchol | Total Panelists |
|---|---|---|---|
| Spice Market | 2 | 4 | 6 |

|  | Without | W/ Pentyl Fenchol | Total Panelists |
|---|---|---|---|
| Spice Market | 1 | 5 | 6 |

|  | Without | W/ Hexyl Fenchol | Total Panelists |
|---|---|---|---|
| Spice Market | 1 | 5 | 6 |

Fig. 2 (Cont.)

| | Without | W/ Heptyl Fenchol | Total Panelists |
|---|---|---|---|
| Spice Market | 1 | 5 | 6 |

| | Without | W/ Octyl Fenchol | Total Panelists |
|---|---|---|---|
| Spice Market | 1 | 5 | 6 |

| | Without | W/ Nonyl Fenchol | Total Panelists |
|---|---|---|---|
| Spice Market | 0 | 6 | 6 |

| | Without | W/ Decyl Fenchol | Total Panelists |
|---|---|---|---|
| Spice Market | 1 | 5 | 6 |

| | Without | W/ Undecyl Fenchol | Total Panelists |
|---|---|---|---|
| Spice Market | 1 | 5 | 6 |

| | Without | W/ Dodecyl Fenchol | Total Panelists |
|---|---|---|---|
| Spice Market | 2 | 4 | 6 |

| | Without | W/ Allyl Fenchol | Total Panelists |
|---|---|---|---|
| Spice Market | 0 | 6 | 6 |

Fig. 2 (Cont.)

|  | Without | W/ (1R)-endo-2-ethyl fenchol | Total Panelists |
|---|---|---|---|
| Spice Market | 0 | 6 | 6 |

|  | Without | W/ (1R)-exo-2-ethyl fenchol | Total Panelists |
|---|---|---|---|
| Spice Market | 0 | 6 | 6 |

|  | Without | W/ (1S)-endo-2-ethyl fenchol | Total Panelists |
|---|---|---|---|
| Spice Market | 0 | 6 | 6 |

|  | Without | W/ (1S)-exo-2-ethyl fenchol | Total Panelists |
|---|---|---|---|
| Spice Market | 0 | 6 | 6 |

Fig. 3

|  | Without | W/ Methyl Fenchol | Total Panelists |
|---|---|---|---|
| Key Lime Coconut | 1 | 5 | 6 |
| Mouthwash | 0 | 6 | 6 |
| Tequila | 1 | 5 | 6 |

|  | Without | W/ Fenchol | Total Panelists |
|---|---|---|---|
| Key Lime Coconut | 2 | 4 | 6 |
| Mouthwash | 1 | 5 | 6 |
| Tequila | 0 | 6 | 6 |

|  | Without | W/ Propyl Fenchol | Total Panelists |
|---|---|---|---|
| Key Lime Coconut | 2 | 4 | 6 |
| Mouthwash | 2 | 4 | 6 |
| Tequila | 1 | 5 | 6 |

|  | Without | W/ Butyl Fenchol | Total Panelists |
|---|---|---|---|
| Key Lime Coconut | 1 | 5 | 6 |
| Mouthwash | 2 | 4 | 6 |
| Tequila | 1 | 5 | 6 |

Fig. 3 (Cont.)

|  | Without | W/ t-Butyl Fenchol | Total Panelists |
|---|---|---|---|
| Key Lime Coconut | 2 | 4 | 6 |
| Mouthwash | 2 | 4 | 6 |
| Tequila | 2 | 4 | 6 |

|  | Without | W/ Pentyl Fenchol | Total Panelists |
|---|---|---|---|
| Key Lime Coconut | 2 | 4 | 6 |
| Mouthwash | 3 | 3 | 6 |
| Tequila | 1 | 5 | 6 |

|  | Without | W/ Hexyl Fenchol | Total Panelists |
|---|---|---|---|
| Key Lime Coconut | 3 | 3 | 6 |
| Mouthwash | 2 | 4 | 6 |
| Tequila | 2 | 4 | 6 |

|  | Without | W/ Heptyl Fenchol | Total Panelists |
|---|---|---|---|
| Key Lime Coconut | 2 | 4 | 6 |
| Mouthwash | 1 | 5 | 6 |
| Tequila | 2 | 4 | 6 |

Fig. 3 (Cont.)

|  | Without | W/ Octyl Fenchol | Total Panelists |
|---|---|---|---|
| Key Lime Coconut | 2 | 4 | 6 |
| Mouthwash | 2 | 4 | 6 |
| Tequila | 2 | 4 | 6 |

|  | Without | W/ Nonyl Fenchol | Total Panelists |
|---|---|---|---|
| Key Lime Coconut | 2 | 4 | 6 |
| Mouthwash | 3 | 3 | 6 |
| Tequila | 2 | 4 | 6 |

|  | Without | W/ Decyl Fenchol | Total Panelists |
|---|---|---|---|
| Key Lime Coconut | 2 | 4 | 6 |
| Mouthwash | 2 | 4 | 6 |
| Tequila | 1 | 5 | 6 |

|  | Without | W/ Undecyl Fenchol | Total Panelists |
|---|---|---|---|
| Key Lime Coconut | 3 | 3 | 6 |
| Mouthwash | 2 | 4 | 6 |
| Tequila | 1 | 5 | 6 |

Fig. 3 (Cont.)

|  | Without | W/ Dodecyl Fenchol | Total Panelists |
|---|---|---|---|
| Key Lime Coconut | 2 | 4 | 6 |
| Mouthwash | 1 | 5 | 6 |
| Tequila | 2 | 4 | 6 |

|  | Without | W/ Allyl Fenchol | Total Panelists |
|---|---|---|---|
| Key Lime Coconut | 1 | 5 | 6 |
| Mouthwash | 1 | 5 | 6 |
| Tequila | 2 | 4 | 6 |

|  | Without | W/ (1R)-endo-2-ethyl fenchol | Total Panelists |
|---|---|---|---|
| Key Lime Coconut | 1 | 5 | 6 |
| Mouthwash | 0 | 6 | 6 |
| Tequila | 1 | 5 | 6 |

|  | Without | W/ (1R)-exo-2-ethyl fenchol | Total Panelists |
|---|---|---|---|
| Key Lime Coconut | 0 | 6 | 6 |
| Mouthwash | 1 | 5 | 6 |
| Tequila | 0 | 6 | 6 |

Fig. 3 (Cont.)

|  | Without | W/ (1S)-endo-2-ethyl fenchol | Total Panelists |
|---|---|---|---|
| Key Lime Coconut | 0 | 6 | 6 |
| Mouthwash | 0 | 6 | 6 |
| Tequila | 0 | 6 | 6 |

|  | Without | W/ (1S)-exo-2-ethyl fenchol | Total Panelists |
|---|---|---|---|
| Key Lime Coconut | 1 | 5 | 6 |
| Mouthwash | 0 | 6 | 6 |
| Tequila | 1 | 5 | 6 |

Fig. 4

|  | w/o | w/ Ethyl Fenchol (1 ppm unless otherwise specified) | Total Panelists |
|---|---|---|---|
| **Cardamom Oil (*5 ppm)** | 1 | 6 | 7 |
| Cinnamon Leaf Oil | 1 | 6 | 7 |
| Clove Leaf Oil | 1 | 6 | 7 |
| Nutmeg Oil | 1 | 6 | 7 |
| Elemi Oil | 1 | 6 | 7 |
| Rosemary Oil | 2 | 5 | 7 |
| Sandalwood Oil Australian | 2 | 5 | 7 |
| Rose Oil Bulgarian | 2 | 5 | 7 |
| Patchouli Oil | 0 | 6 | 6 |
| Clearwood Oil | 1 | 6 | 7 |
| Cashmeran | 1 | 6 | 7 |
| Lemon Oil | 2 | 5 | 7 |
| Ginger Oil | 2 | 5 | 7 |
| Methyl Ionone 95% | 0 | 5 | 5 |
| Methyl Ionone 70% | 1 | 6 | 7 |

COMPOSITIONS CONTAINING FENCHOLS AND METHODS OF USE

RELATED APPLICATION

This application claims the benefit of U.S. Application No. 62/932,951, filed Nov. 8, 2019, which is incorporated herein by reference in its entirety.

BACKGROUND OF THE DISCLOSURE

1. Field of the Disclosure

This disclosure relates to compositions containing fenchols (i.e., alkylated fenchols, isomeric, diastereomeric or enantiomeric alkylated fenchols, or mixtures thereof), and to methods of enhancing odor strength or olfactive character of a composition.

2. Description of the Related Art

There has been considerable work performed relating to substances which can be used to modify, augment or enhance odors, for example, flavors and fragrances, to (or in) various consumer products. These substances can be used to diminish the use of natural materials, some of which may be in short supply, and to provide more uniform properties in the finished product.

These substances can also allow for increased perception of a material (e.g., a natural oil), thereby perhaps requiring less of the more expensive natural oil in a consumer product, and resulting in cost savings.

In P. Gosselin et al., Tetrahedron Letters, Vol. 31, No. 22, pp. 3151-3154, 1990, several stereoselective routes to both ethyl α-fenchols and ethyl β-fenchols are discussed. Direct addition of ethyllithium to fenchone was the best route to ethyl α-fenchols whereas obtention of ethyl β-fenchols was achieved through the highly stereoselective retroethynylation of a mixture of ethynyl α-fenchols and ethynyl β-fenchols.

In Barbara Finato et al., J. Agric. Food Chem. 1992, 40, 857-859, several derivatives of cyclohexanol and fenchol were synthesized, as structural models of geosmin, with the aim to provide cheap earthy odorants. 1,2,2,6-Tetramethylcyclohexanol and 1-ethyl-2,2,6-trimethylcyclohexanol had odors very similar to that of geosmin. All of the compounds were synthesized in one step from cheap and readily available ketones, by reaction with Grignard or lithium derivatives. The products obtained from the two enantiomeric forms of fenchone exhibited different odors.

There remains a need and demand for substances which can be used to enhance odors, for example, flavors and fragrances in various consumer products, especially odor enhancers that can result in cost savings.

The present disclosure provides many advantages, including access to novel and exciting odor enhancers, which shall become apparent as described below.

SUMMARY OF THE DISCLOSURE

This disclosure relates in part to compositions containing fenchols (i.e., alkylated fenchols, isomeric, diastereomeric or enantiomeric alkylated fenchols, or mixtures thereof), and to methods of enhancing odor strength or olfactive character of a composition.

This disclosure also relates in part to a composition comprising: (i) at least one material having odor strength or olfactive character; and (ii) at least one fenchol. The at least one fenchol is selected from an alkylated fenchol, an isomeric, diastereomeric or enantiomeric alkylated fenchol, or mixtures thereof. The at least one fenchol is present in an amount effective to enhance odor strength or olfactive character of the composition.

This disclosure further relates in part to a synergistic composition comprising: (i) at least one material having odor strength or olfactive character; and (ii) at least one fenchol. The at least one fenchol is selected from an alkylated fenchol, an isomeric, diastereomeric or enantiomeric alkylated fenchol, or mixtures thereof. The at least one fenchol is present in an amount effective to enhance odor strength or olfactive character of the composition. The synergistic combination of the at least one material having odor strength or olfactive character and the at least one fenchol produces a combined effect greater than the sum of their separate effects for odor strength or olfactive character.

This disclosure yet further relates in part to a method of enhancing odor strength or olfactive character of a composition. The composition comprises: (i) at least one material having odor strength or olfactive character; and (ii) at least one fenchol. The at least one fenchol is selected from an alkylated fenchol, an isomeric, diastereomeric or enantiomeric alkylated fenchol, or mixtures thereof. The method comprises adding the at least one fenchol to the at least one material having odor strength or olfactive character in an amount effective to enhance odor strength or olfactive character of the composition.

This disclosure also relates in part to a consumer product containing a composition comprising: (i) at least one material having odor strength or olfactive character; and (ii) at least one fenchol. The at least one fenchol is selected from an alkylated fenchol, an isomeric, diastereomeric or enantiomeric alkylated fenchol, or mixtures thereof. The at least one fenchol is present in an amount effective to enhance odor strength or olfactive character of the consumer product.

In accordance with this disclosure, it has been surprisingly found that fenchols (i.e., alkylated fenchols, isomeric, diastereomeric or enantiomeric alkylated fenchols, or mixtures thereof) can be added to a material having odor strength or olfactive character (e.g., flavor or fragrance material) in an amount effective to enhance odor strength or olfactive character of the material.

Further, it has been surprisingly found that fenchols (i.e., alkylated fenchols, isomeric, diastereomeric or enantiomeric alkylated fenchols, or mixtures thereof) can be added to a material having odor strength or olfactive character (e.g., flavor or fragrance material) in an amount effective to synergistically enhance odor strength or olfactive character of the material.

Further objects, features and advantages of the present disclosure will be understood by reference to the following detailed description.

BRIEF DESCRIPTION OF THE DRAWINGS

FIG. 1 shows the results of blotter selections by panelists in which the blotters were materials having odor strength or olfactive character (e.g., rosemary essential oil, nutmeg essential oil, Clearwood bio-based material, Patchouli essential oil and a natural/synthetic mixture) with or without fenchols (e.g., fenchol, methyl fenchol and 2-ethyl fenchol), in accordance with the Examples.

FIG. 2 shows spice market fragrance materials prepared with or without fenchols, and results from panelists presented with the spice market fragrance to determine which they feel is stronger in a comparison of fragrance without fenchols versus fragrance with various fenchols, in accordance with the Examples.

FIG. 3 shows key lime coconut, mouthwash and tequila flavor materials prepared with or without fenchols, and results from panelists presented with the key lime coconut, mouthwash and tequila flavor to determine which they feel is stronger in a comparison of flavor without fenchols versus flavor with various fenchols, in accordance with the Examples.

FIG. 4 shows various essential oil fragrance materials prepared with or without ethyl fenchol, and results of panelists presented with the essential oil fragrance to determined which they felt was stronger in a comparison of essential oil fragrance without ethyl fenchol versus essential oil fragrance with ethyl fenchol, in accordance with the Examples.

DESCRIPTION OF THE PREFERRED EMBODIMENTS

As used herein, "fenchols" refers to alkylated fenchols, isomeric, diastereomeric or enantiomeric alkylated fenchols, and mixtures thereof.

In an embodiment, the alkylated fenchols can be represented by the formula

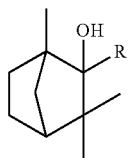

(I)

wherein R is a substituted or unsubstituted, branched or straight chain, alkyl or alkene group having from 1 to about 20 carbon atoms; including isomers, diastereomers and enantiomers of the fenchols of structure (I).

Preferably, in the alkylated fenchols of structure (I), R is methyl, ethyl, propyl, butyl, tert-butyl, pentyl, hexyl, heptyl, octyl, nonyl, decyl, undecyl, dodecyl, allyl or vinyl.

Illustrative alkylated fenchols useful in the compositions of this disclosure having at least one material having odor strength or olfactive character (e.g., flavor or fragrance material) include, for example, methyl fenchol, 2-ethyl fenchol, propyl fenchol, butyl fenchol, tert-butyl fenchol, pentyl fenchol, hexyl fenchol, heptyl fenchol, octyl fenchol, nonyl fenchol, decyl fenchol, undecyl fenchol, dodecyl fenchol, allyl fenchol, vinyl fenchol, and mixtures thereof. The alkylated fenchols are added to the material having odor strength or olfactive character in an amount effective to enhance odor strength or olfactive character of the material.

In an embodiment, preferred isomeric, diastereomeric or enantiomeric alkylated fenchols can be represented by the formula

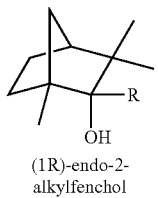 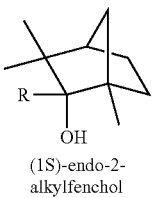 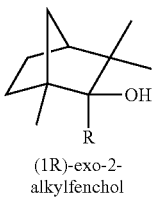

(1R)-endo-2-alkylfenchol  (1S)-endo-2-alkylfenchol  (1R)-exo-2-alkylfenchol

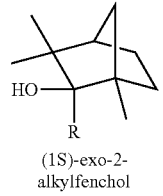

(1S)-exo-2-alkylfenchol wherein R is a substituted or unsubstituted, branched or straight chain, alkyl or alkene group having from 1 to about 20 carbon atoms.

Preferably, in the isomeric, diastereomeric or enantiomeric alkylated fenchols, R is methyl, ethyl, propyl, butyl, tert-butyl, pentyl, hexyl, heptyl, octyl, nonyl, decyl, undecyl, dodecyl, allyl or vinyl.

Illustrative isomeric, diastereomeric or enantiomeric alkylated fenchols useful in the compositions of this disclosure having at least one material having odor strength or olfactive character (e.g., flavor or fragrance material) include, for example, (1R)-endo-2-methyl fenchol, (1R)-exo-2-methyl fenchol, (1S)-endo-2-methyl fenchol, (1S)-exo-2-methyl fenchol, (1R)-endo-2-ethyl fenchol, (1R)-exo-2-ethyl fenchol, (1S)-endo-2-ethyl fenchol, (1S)-exo-2-ethyl fenchol, (1R)-endo-2-propyl fenchol, (1R)-exo-2-propyl fenchol, (1S)-endo-2-propyl fenchol, (1S)-exo-2-propyl fenchol, (1R)-endo-2-butyl fenchol, (1R)-exo-2-butyl fenchol, (1S)-endo-2-butyl fenchol, (1S)-exo-2-butyl fenchol, (1R)-endo-2-tert-butyl fenchol, (1R)-exo-2-tert-butyl fenchol, (1S)-endo-2-tert-butyl fenchol, (1S)-exo-2-tert-butyl fenchol, (1R)-endo-2-pentyl fenchol, (1R)-exo-2-pentyl fenchol, (1S)-endo-2-pentyl fenchol, (1S)-exo-2-pentyl fenchol, (1R)-endo-2-hexyl fenchol, (1R)-exo-2-hexyl fenchol, (1S)-endo-2-hexyl fenchol, (1S)-exo-2-hexyl fenchol, (1R)-endo-2-heptyl fenchol, (1R)-exo-2-heptyl fenchol, (1S)-endo-2-heptyl fenchol, (1S)-exo-2-heptyl fenchol, (1R)-endo-2-octyl fenchol, (1R)-exo-2-octyl fenchol, (1S)-endo-2-octyl fenchol, (1S)-exo-2-octyl fenchol, (1R)-endo-2-nonyl fenchol, (1R)-exo-2-nonyl fenchol, (1S)-endo-2-nonyl fenchol, (1S)-exo-2-nonyl fenchol, (1R)-endo-2-decyl fenchol, (1R)-exo-2-decyl fenchol, (1S)-endo-2-decyl fenchol, (1S)-exo-2-decyl fenchol, (1R)-endo-2-undecyl fenchol, (1R)-exo-2-undecyl fenchol, (1S)-endo-2-undecyl fenchol, (1S)-exo-2-undecyl fenchol, (1R)-endo-2-dodecyl fenchol, (1R)-exo-2-dodecyl fenchol, (1S)-endo-2-dodecyl fenchol, (1S)-exo-2-dodecyl fenchol, (1R)-endo-2-vinyl fenchol, (1R)-exo-2-vinyl fenchol, (1S)-endo-2-vinyl fenchol, (1S)-exo-2-vinyl fenchol, (1R)-endo-2-allyl fenchol, (1R)-exo-2-allyl fenchol, (1S)-endo-2-allyl fenchol, (1S)-exo-2-allyl fenchol, and mixtures thereof. The isomeric, diastereomeric or enantiomeric alkylated fenchols are added to the material having odor strength or olfactive character in an amount effective to enhance odor strength or olfactive character of the material.

Mixtures of at least one alkylated fenchol and at least one isomeric, diastereomeric or enantiomeric alkylated fenchol are useful in the compositions of this disclosure having at least one material having odor strength or olfactive character (e.g., flavor or fragrance material). The mixtures of at least one alkylated fenchol and at least one isomeric, diastereomeric or enantiomeric alkylated fenchol are added to the material having odor strength or olfactive character in an amount effective to enhance odor strength or olfactive character of the material.

In an embodiment, the fenchols include C1-C12 alkylated fenchols or mixtures thereof, or C1-C12 isomeric, diastereomeric or enantiomeric alkylated fenchols or mixtures thereof, or mixtures of C1-C12 alkylated fenchols and C1-C12 isomeric, diastereomeric or enantiomeric alkylated fenchols.

As used herein, "material(s) having odor strength or olfactive character" refers to natural oils, bio-based materials, synthetic materials, flavor materials, fragrance materials, and the like. Any materials capable of having odor strength or olfactive character enhanced are included within the scope of this disclosure.

In an embodiment, preferred materials having odor strength or olfactive character include, for example, essential oils, single or compounded synthetic materials, flavor materials, fragrance materials, and the like.

Illustrative natural or essential oils useful in this disclosure include, for example, Patchouli essential oil, and the like.

Illustrative bio-based materials useful in this disclosure include, for example, Clearwood™ bio-based oil (Firmenich), and the like.

Illustrative synthetic materials, including single or compounded synthetic materials, useful in this disclosure include, for example, Safraleine™ (2,3,3-trimethyl-2H-inden-1-one (Givaudan), and the like.

In an embodiment, as used herein, fragrance materials or compositions refers to mixtures comprising one or more fragrance components, in any of their forms, and one or more solvents or perfuming co-ingredients. As known in the art, a fragrance composition will contain one or more fragrance components (e.g., perfuming co-ingredients) in order to impart an olfactory note to the composition (e.g., a household cleaner, perfume, or other commercial product) to which it is added. In one embodiment, the fragrance composition contains two or more fragrance components which, collectively and in combination with the solvent to which they are added, impart an intended olfactory note (e.g., a hedonically pleasing note) to a human in close proximity to the fragrance composition.

In general terms, perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils of natural or synthetic origin, and are known to perfumers of ordinary skill in the art.

Fragrance materials and mixtures of fragrance materials which can be used in combination with the fenchols according to this disclosure for manufacturing perfume compositions are, for example, natural products, such as essential oils, absolutes, resinoids, resins, concretes, etc., but also synthetic fragrance materials such as hydrocarbons, alcohols, aldehydes, ketones, ethers, acids, esters, acetals, ketals, nitriles, etc., including saturated and unsaturated compounds, aliphatic carbocyclic and heterocyclic compounds.

Examples of fragrance materials which can be used in combination with the fenchols according to the disclosure include geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexyl-cinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-ol, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, aromatic nitromusks, and the like to mention a few.

Auxiliary substances and solvents which can be used in perfume compositions which contain fenchols according to this disclosure include, for example: ethanol, isopropanol, dipropylene glycol, dipropyleneglycol monomethyl ether, diethylphthalate, and the like.

The perfumery compositions of this disclosure may be compounded according to recognized techniques of perfumery employing known odiferous perfumery ingredients. Specific natural odoriferous ingredients which may be blended with the materials of disclosure include vetivert oil, guaiac wood oil, lemon oil, rose absolute, jasmin absolute, geranium oil, lavandin oil, patchouli oil, petitgrain oil, bergamot oil, clove bud oil, bay oil, nutmeg oil, pimento berry oil, ylang oil, sandalwood oil, clary sage oil, labdanum resin, orange oil, olibanum resin, mandarin oil, neroli oil, oakmoss, cedarwood oil and many others known to perfumers.

In an embodiment, as used herein, perfume materials or compositions refers to mixtures of fragrance materials and optionally auxiliary substances, dissolved in a suitable solvent or mixed with a powdery substrate which is used to impart a desired odor to the skin and/or all types of products. Examples of such products include fine fragrance and consumer products including, but not limited to, soaps, detergents, air fresheners, room sprays, candles, cosmetics, such as creams, ointments, toilet waters, pre- and aftershave lotions, talcum powders, hair-care products, body deodorants and anti-perspirants.

In an embodiment, as used herein, flavor materials or compositions refers to materials or compositions that contain one or more compound(s) (e.g., co-ingredients) that provide(s) a desired taste when combined with a solvent that is suitable for oral administration and oral consumption. The skilled person in the art of flavors is able to select these materials on the basis of general knowledge and according to the nature of the product to be flavored and the desired taste.

In particular, flavor materials or compositions refers to mixtures of flavor materials and optionally auxiliary substances, dissolved in a suitable solvent or mixed with a powdery substrate which is used to impart a desired taste to all types of products. Examples of such products include beverages, dairy products, confectionaries, cereals, snacks, soups and the like.

As used herein, the phrase "consumer product" refers to composition that is in a form ready for use by the consumer for the marketed indication. A solvent suitable for use in a consumer product is a solvent that, when combined with other components of the end product, will not render the consumer product unfit for its intended consumer use.

Any one of the fenchols of this disclosure can be included in a fragrance or flavor composition. In one embodiment, any one of the fenchols of this disclosure is provided in a fragrance composition. In an alternative embodiment, any one of the fenchols of this disclosure is provided in a flavor composition.

As described herein, this disclosure relates to a composition comprising at least one fenchol. The at least one fenchol is selected from an alkylated fenchol, an isomeric, diastereomeric or enantiomeric alkylated fenchol, or mixtures thereof. The at least one fenchol is present in an amount effective to enhance odor strength or olfactive character of the composition.

In an embodiment, as described herein, this disclosure relates to a fragrance or flavor composition comprising at least one fenchol. The at least one fenchol is selected from an alkylated fenchol, an isomeric, diastereomeric or enantiomeric alkylated fenchol, or mixtures thereof. The at least one fenchol is present in an amount effective to enhance odor strength or olfactive character of the composition.

For the compositions of this disclosure, the at least one fenchol is present in an amount of from about 0.1 ppb to about 1000 ppm by weight, based on the total weight of the composition, to enhance odor strength or olfactive character of the composition.

In an embodiment, for the compositions of this disclosure, the at least one fenchol is present in an amount of from about 0.1 ppb to about 500 ppm by weight, based on the total weight of the composition, to enhance odor strength or olfactive character of the composition.

In an embodiment, for the compositions of this disclosure, the at least one fenchol is present in an amount of at least about 1 ppm by weight, based on the total weight of the composition, to enhance odor strength or olfactive character of the composition.

In an embodiment, for the fragrance compositions of this disclosure, the at least one fenchol is present in an amount of at least about 1 ppm by weight, based on the total weight of the composition, to enhance odor strength or olfactive character of the composition.

In an embodiment, for the flavor compositions of this disclosure, the at least one fenchol is present in an amount of at least about 0.1 ppm by weight, based on the total weight of the composition, to enhance the olfactive character, taste or strength of the composition.

For the fragrance compositions of this disclosure, the at least one fenchol can be combined with geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloromethylphenyl carbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentyl-cyclopentane, 2-n-heptylcyclopentanone, 3-methyl-2-pentyl-2-cyclopentenone, n-decanal, n-dodecanal, 9-decen-1-ol, phenoxyethylisobutyrate, phenylacetaldehyde-dimethylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, or aromatic nitromusks, to impart a fragrance to the composition.

For the flavor compositions of this disclosure, the at least one fenchol can be combined with geraniol, geranyl acetate, linalool, linalyl acetate, citronellol, citronellyl acetate, terpineol, terpinyl acetate, 2-phenylethanol, 2-phenylethyl acetate, benzyl alcohol, benzyl acetate, benzyl salicylate, heliotropine, benzaldehyde, anisaldehyde, benzyl salicylate, e, n-decanal, n-dodecanal, 9-decen-1-ol, coumarin, eugenol, vanillin, hexanal, eucalyptol, ionones, methylionones, isomethylionones, irones, cis-3-hexenol and esters of the latter, acetaldehyde, ethyl acetate, ethyl butyratecinnamic aldehyde, cuminic aldehyde, furfural, cinnamic aldehyde, maltol, ethyl maltol, dimethyl sulfide, gamma decalactone, gamma undecalactone, diacetyl, ethyl valerate, damascone, damascenone, methyl caproate, cyclotene, butyric acid, acetoin, delta decalactone, furaneol, acetoin, benzodihydro pyrone, 2,6-nonadienal, melonal or methyl heptane carbonate, to impart a flavor to the composition.

In accordance with this disclosure, the fenchols of this disclosure can be prepared by conventional processes. The compositions of this disclosure can also be prepared by conventional processes.

As described herein, this disclosure provides a consumer product containing a composition comprising: (i) at least one material having odor strength or olfactive character; and (ii) at least one fenchol. The at least one fenchol is selected from an alkylated fenchol, an isomeric, diastereomeric or enantiomeric alkylated fenchol, or mixtures thereof. The at least one fenchol is present in an amount effective to enhance odor strength or olfactive character of the consumer product.

Illustrative consumer fragrance products useful in this disclosure include, for example, a candle, an air care product, a perfume, a cologne, a soap, a personal care product, a detergent, a fabric care product, a household cleaning product, and the like.

More particularly, illustrative consumer fragrance products include a soap, a detergent, an air freshener, a room spray, a pomander, a candle, and a cosmetic comprising a cream, an ointment, a toilet water, a pre-shave lotion, an aftershave lotion, a talcum powder, a hair-care agent, a body deodorant, and an anti-perspirant.

Preferred illustrative consumer fragrance products include an air care product, laundry care, a perfume, and a cologne.

In an embodiment, one or more of the fenchols of the present disclosure, alone or in combination with other co-ingredients, can be employed in fragrance compositions, solvents, media and the like. As indicated herein, the use of such fenchols is applicable to a wide variety of products in the fragrance industry such as, but not limited to: candles; air fresheners; perfumes; colognes; personal care products such as soaps, deodorants, shampoos, conditioners, shower gels and shaving lotions; cosmetics such as lotions and ointments; as well as detergents; fabric care products and household cleaner/cleaning agents.

As the fenchols of the present disclosure are useful ingredients for the perfuming of various products, the present disclosure also concerns all different forms of the fenchols that can be advantageously employed in perfumery. Such forms include a composition including fenchols and a solvent commonly used in perfumery compositions. Examples of such solvents used in perfumery are known in the art and include, but are not limited to: dipropyleneglycol, diethyl phthalate, isopropyl myristate, benzyl benzoate, 2-(2-ethoxy)-1-ethanol, ethyl citrate, ethanol, water/ethanol mixtures, limonene or other terpenes, isoparaffins such as those known under the trademark Isopar™ (ExxonMobil Chemicals, Houston, Tex.), and glycol ethers and glycol ether esters such as those known under the trademark Dowanol™ (Dow Chemical Company, Midland Mich.).

In an embodiment, for fragrance applications, typical concentrations of the fenchols are on the order of 0.01 ppm to 1% by weight, or more, based on the total weight of the composition into which the fragrance compound is incorporated. Those skilled in the art will be able to employ the desired level of the compounds of the disclosure to provide the desired fragrance and intensity. In general, the fenchols of the present disclosure will be used in relatively small amounts, typically via significant dilutions due to their high-impact, diffusive properties.

The perfuming compositions according to the disclosure may be in the form of a simple mixture of the various co-ingredients and solvents, or also in the form of a biphasic system such as an emulsion or microemulsion. Such systems are well-known to persons skilled in the art.

As described herein, suitable perfumed end products that can include a composition of the present disclosure including, but are not limited to: 1) candles, air fresheners, perfumes and colognes, 2) personal care products such as soaps, deodorants, shampoos, conditioners, shower gels and shaving lotions; 3) cosmetics such as lotions and ointments; as well as 4) detergents, fabric care products and household cleansers/cleaning agents. Depending on the solvents that may be present in some end products, it may be necessary to protect the fenchols from premature degradation, for example by encapsulation or with a stabilizer, or other methods well-known to those of ordinary skill in the art.

The compositions of the present disclosure can also be added to, for example: 1) fragrance products; perfume; eau de perfume; eau de toilet; eau de cologne; and the like; skin-care cosmetics, face washing creams, varnishing creams, cleansing creams, cold creams, massage creams and oils, milky lotions, skin toning lotion, cosmetic solutions, packs, makeup remover, and the like; 2) makeup cosmetics, foundations, face powders, pressed powders, talcum powders, lip sticks, lip creams, cheek powders, eyeliners, mascara, eye shadows, eyebrow pencils, eye packs, nail enamels, nail enamel removers, and the like; 3) hair care cosmetics, pomades, brilliantines, setting lotions, hair sticks, hair solids, hair oils, hair treatments, hair creams, hair tonics, hair liquids, hair sprays, hair restorers, hair dyes, and the like; 4) sunburn cosmetics, suntan products, sunscreen products, and the like; 5) medical cosmetics, antiperspirants, after-shave lotions and gels, permanent wave lotions, medicated soaps, medicated shampoos, medicated skin care products, and the like; 6) hair care products, shampoos, rinses, shampoo-including-rinses, hair conditioners, hair treatments, hair packs, and the like; 7) as soaps, toilet soaps, bath soaps, perfumed soaps, transparent soaps, synthetic soaps, and the like; 8) body washing soaps, body soaps, body shampoos, hand soaps, and the like; 9) bathing, bathing agents (e.g., bath salts, bath tablets, bath liquids, and the like), foam baths (bubble bath and the like), bath oils (e.g., bath perfumes, bath capsules and the like), milk baths, bath gels, bath cubes, and the like; 10) detergents, heavy duty detergents for clothes, light duty detergents for clothes, liquid detergents, laundering soaps, compact detergents, powder soaps, and the like; 11) softening finishing agents, softeners, furniture care products, and the like; and deodorants, aromatic substances and the like; and 12) insect repellent, insecticides, and the like.

Fragrances in consumer products provide several functions. They mask base odors, provide aesthetic pleasure and signal product attributes and function to the user, e.g., hygiene, cleanliness, mildness. Notwithstanding these benefits, it is also true that perfumes can cause a myriad of problems within products they have been added to, e.g., discoloration, phase separation, problems such as irritation and occasional allergic reaction to the user. Additionally, fragrances represent one of the more expensive components of the product and many fragrance ingredients may not be easily biodegradable. Over the years, perfume levels in many consumer products have increased by the popular demand but at the same time consumers have also become more critical of the fragranced products they purchase and use.

Therefore, in an embodiment, this disclosure provides high intensity consumer acceptable fragrances and desirable hedonics at a much lower concentration than achieved before. This lowering of fragrance concentration in consumer products by an order of magnitude has the benefit of cost saving, less interference with the physical properties of the product base, minimizing toxicological implications on the user, and lowering the environmental impact of chemicals used.

The quantities in which the compositions of this disclosure can be used in perfume compositions or in products to be perfumed can vary within wide limits and depend inter alia on the nature of the product in which the fragrance material is used, on the nature and quantity of the other components in the perfume composition and on the odor effect which is aimed at. It is therefore only possible to specify very rough limits, which, however, provide sufficient information for the specialist to be able to use the fenchols according to the disclosure independently. In most cases a quantity of only 1 ppm in a perfume composition will already be sufficient to obtain a clearly perceptible odor effect. On the other hand, to achieve special odoriferous effects it is possible to use quantities of 100, 1000, 5000 ppm or even more in a composition. In products perfumed with such compositions, these concentrations are proportionately lower, depending on the quantity of composition used in the product.

There are three basic stages of a fragrance. The first stage (i.e., top notes) is the first impression that a fragrance gives to a customer. This initial stage is the most volatile. In the second stage (i.e., middle notes), a few moments after the application of a fragrance, the heart is revealed. This modifying part of the fragrance has medium volatility. In the third stage (i.e., base notes), after a fragrance dries down, these notes are more pronounced. This part of the fragrance is the longest lasting. The balance between these three groups is very important. In a well-balanced fragrance, it is important to understand what group or groups are the most important for a particular application. The fragrance compositions of this disclosure exemplify a desirable balance between these three groups for desired applications.

Illustrative consumer flavor products useful in this disclosure include, for example, a beverage, a powder or semi-frozen/frozen concentrate for a drink, a candy, a sugarless candy, a chocolate, a chewing gum, a bubble gum, a condiment, a spice, a seasoning, a dry cereal, an oatmeal, a granola bar, an alcoholic beverage, an energy beverage, a juice, a tea, a coffee, a salsa, a gel bead, a film strip for halitosis, a lozenge, a cough drop, a throat lozenge, a throat spray, a toothpaste, and a mouth rinse.

More particularly, illustrative consumer flavor products include a beverage, a dairy product, a confectionary, a cereal, a snack, and a soup.

Preferred illustrative consumer flavor products include a beverage, a chewing gum, and a bubble gum.

In an embodiment, one or more of the fenchols of the present disclosure, alone or in combination with other co-ingredients, can be employed in fragrance and flavor compositions, solvents, media and the like. As indicated herein, the use of such fenchols is applicable to a wide variety of products in the fragrance industry such as, but not limited to: candles; air fresheners; perfumes; colognes; personal care products such as soaps, deodorants, shampoos, conditioners, shower gels and shaving lotions; cosmetics such as lotions and ointments; as well as detergents; fabric care products and household cleaner/cleaning agents. Also, as indicated herein, the use of such fenchols is also applicable to a wide variety of products in the flavor industry such as, but not limited to: foodstuffs such as baked goods, dairy products, desserts, etc.; beverages such as juices, sodas, teas, flavored waters, fruit-based "smoothy" drinks, milk-based drinks, etc.; confectionaries such as sweets, hard candy, gums; and gelatinous materials, snacks, desserts, pharmaceuticals, oral care products and the like.

As the fenchols of the present disclosure are useful ingredients for the perfuming or flavoring of various products, the present disclosure also concerns all different forms of the fenchols that can be advantageously employed in perfumery or in flavors. Such forms include a composition including fenchols and a solvent commonly used in perfumery or in flavor compositions. Examples of such solvents used in perfumery are known in the art and include, but are not limited to: dipropyleneglycol, diethyl phthalate, isopropyl myristate, benzyl benzoate, 2-(2-ethoxy)-1-ethanol, ethyl citrate, ethanol, water/ethanol mixtures, limonene or other terpenes, isoparaffins such as those known under the trademark Isopar™ (ExxonMobil Chemicals, Houston, Tex.), and glycol ethers and glycol ether esters such as those known under the trademark Dowanol™ (Dow Chemical Company, Midland Mich.). Examples of solvents commonly used in flavors are also known in the art and include, but are not limited to: propylene glycol, triacetin, triethyl citrate, benzyl alcohol, benzyl benzoate, ethanol, vegetable oils and terpenes.

In an embodiment, for fragrance applications, typical concentrations of the fenchols are on the order of 0.01 ppm to 1% by weight, or more, based on the total weight of the composition into which the fragrance compound is incorporated. Those skilled in the art will be able to employ the desired level of the fenchols of the disclosure to provide the desired fragrance/flavor intensity. In general, the fenchols of the present disclosure will be used in relatively small amounts, typically via significant dilutions due to their high-impact, diffusive properties.

The perfuming compositions according to the disclosure may be in the form of a simple mixture of the various co-ingredients and solvents, or also in the form of a biphasic system such as an emulsion or microemulsion. Such systems are well-known to persons skilled in the art.

As described herein, suitable perfumed end products that can include a composition of the present disclosure including, but are not limited to: 1) candles, air fresheners, perfumes and colognes, 2) personal care products such as soaps, deodorants, shampoos, conditioners, shower gels and shaving lotions; 3) cosmetics such as lotions and ointments; as well as 4) detergents, fabric care products and household cleansers/cleaning agents. Depending on the solvents that may be present in some end products, it may be necessary to protect the fenchols from premature degradation, for example by encapsulation or with a stabilizer, or other methods well-known to those of ordinary skill in the art.

The compositions of the present disclosure can also be added to, for example: 1) fragrance products; perfume; eau de perfume; eau de toilet; eau de cologne; and the like; skin-care cosmetics, face washing creams, varnishing creams, cleansing creams, cold creams, massage creams and oils, milky lotions, skin toning lotion, cosmetic solutions, packs, makeup remover, and the like; 2) makeup cosmetics, foundations, face powders, pressed powders, talcum powders, lip sticks, lip creams, cheek powders, eyeliners, mascara, eye shadows, eyebrow pencils, eye packs, nail enamels, nail enamel removers, and the like; 3) hair care cosmetics, pomades, brilliantines, setting lotions, hair sticks, hair solids, hair oils, hair treatments, hair creams, hair tonics, hair liquids, hair sprays, hair restorers, hair dyes, and the like; 4) sunburn cosmetics, suntan products, sunscreen products, and the like; 5) medical cosmetics, antiperspirants, after-shave lotions and gels, permanent wave lotions, medicated soaps, medicated shampoos, medicated skin care products, and the like; 6) hair care products, shampoos, rinses, shampoo-including-rinses, hair conditioners, hair treatments, hair packs, and the like; 7) as soaps, toilet soaps, bath soaps, perfumed soaps, transparent soaps, synthetic soaps, and the like; 8) body washing soaps, body soaps, body shampoos, hand soaps, and the like; 9) bathing, bathing agents (e.g., bath salts, bath tablets, bath liquids, and the like), foam baths (bubble bath and the like), bath oils (e.g., bath perfumes, bath capsules and the like), milk baths, bath gels, bath cubes, and the like; 10) detergents, heavy duty detergents for clothes, light duty detergents for clothes, liquid detergents, laundering soaps, compact detergents, powder soaps, and the like; 11) softening finishing agents, softeners, furniture care products, and the like; and deodorants, aromatic substances and the like; 12) insect repellent, insecticides, and the like; 13) oral care products such as tooth pastes, mouth cleaners, mouth wash, troches, chewing gums, and the like; and 14) pharmaceutical products, poultices, external skin care pharmaceuticals such as ointments, internal administration medicines, and the like.

Furthermore, the compositions of the disclosure, in any of their forms, can also be incorporated into flavoring compositions or flavored products, together with co-ingredients or adjuvants. Consequently, the use of the compositions of the present disclosure, in any of their forms, as flavoring ingredients, is another object of the present disclosure, as is a flavor composition comprising a fenchol of the present disclosure.

The flavor compositions according to the disclosure may be in the form of a simple mixture of flavoring ingredients or in an encapsulated form, e.g., a flavoring composition entrapped into a solid matrix that may comprise wall-forming and plasticizing materials such as mono-, di- or trisaccharides, natural or modified starches, hydrocolloids, cellulose derivatives, polyvinyl acetates, polyvinylalcohols, proteins or pectins. Examples of particularly useful matrix materials include, for example, sucrose, glucose, lactose, levulose, fructose, maltose, ribose, dextrose, isomalt, sorbitol, mannitol, xylitol, lactitol, maltitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylinethyl cellulose, derivatives, gelatin, agar, alginate and mixtures thereof. Encapsulation is well-known to persons skilled in the art, and may be performed, for instance, using techniques such as spray-drying, agglomeration or extrusion, or coating encapsulation, including coacervation and complex coacervation techniques.

For flavor applications, typical concentrations of fenchols are of the order of 0.1 ppb-100 ppm. Preferably, applicable concentrations fall in the range of 0.001 ppm-0.01 ppm. Those skilled in the art will be able to employ the desired level of the fenchols to provide the desired flavor and intensity. Much higher concentrations may be employed when the compounds are used in concentrated flavors and flavor compositions.

In an embodiment, a composition of the present disclosure is used in chewing and bubble gums and confectionaries (e.g., hard or soft candies or lozenges). Chewing gum compositions typically include one or more gum bases and other standard components such as flavoring agents, softeners, sweeteners and the like. Flavoring agents for use in chewing gum compositions are well known and include natural flavors such as citrus oils, peppermint oil, spearmint oil, oil of wintergreen, natural menthol, cinnamon, ginger and the like; artificial flavors such as menthol, carvone, limonene, cinnamic aldehyde, linalool, geraniol, ethyl butyrate, and the like. As is known in the art, the ingredients used in chewing gum compositions can include sweeteners, both natural and artificial and both sugar and sugarless. Sweeteners are typically present in the chewing gum compositions in amounts of from about 20% to 80% by weight, preferably from about 30% to 60% by weight, based on the total weight of the chewing gum composition. Sugarless sweeteners include, but are not limited sugar alcohols such as Sorbitol, manifold, xylitol, hydrogenated starch hydrolysates, malitol and the like. High intensity sweeteners such as sucralose, aspartame, neotame, salts of acesulfame, and the like, when employed, are typically present up to about 1.0% by weight.

In an alternative embodiment, a composition of the present disclosure is included in an oral personal care product (e.g., a mouthwash or toothpaste). For example, a mouthwash can be prepared by dissolving a flavor composition (e.g., a flavor cocktail) (liquid or powder) that includes a composition of the present disclosure in a solvent (e.g., water) that further includes, for example, a flavor such as menthol and a surfactant; and then mixing the resulting solution with, for example, an aqueous erythritol solution.

In one embodiment of the present disclosure, a composition of the present disclosure is added, directly or indirectly, to a pharmaceutical dosage form (e.g., a tablet, capsule, drop or lozenge) that contains a therapeutically active agent (e.g., a medicament). For example, one embodiment of the present disclosure provides a cough drop or lozenge containing one or more compositions of the present disclosure and, optionally, further containing menthol or other medicaments for the treatment of sore throat, coughing or other upper respiratory ailments.

One or more of the present compositions can also be added to, for example, compositions for the preparation of: 1) carbonated or non-carbonated fruit beverages, carbonated cola drinks, wine coolers, fruit liquors, cordials, milk drinks, smoothy drinks, flavored water, tropical alcoholic and "virgin" drink mixes (e.g. margarita, pina colada or "rum-runner" concentrates), and powders for drinks (e.g., powdered sports or "hydrating" drinks); 2) frozen confectioneries such as ice creams, sherbets, and ice-lollies, hard candies, soft candies, taffies, chocolates, and sugarless candies; 3) desserts such as jelly and pudding; 4) confectioneries such as cakes, cookies, chewing gums and bubble gums; 5) condiments, spices and seasonings, dry cereals, oatmeals, and granola bars; 6) alcoholic beverages, energy beverages, juices, teas, coffees, salsa, and gel beads; 7) film strips for halitosis, and oral personal care products; 8) gelatin candies, pectin candies, starch candies, lozenges, cough drops, throat lozenges, throat sprays, and toothpastes.

The present compositions may also be added to, for example; 1) confectioneries such as buns with jam filling, and bars of sweet jellied paste; 2) jams; candies; 3) breads; 4) beverages such as green tea, oolong tea, black tea, persimmon leaf tea, Chamomile tea, *Sasa veitchii* tea, mulberry leaf tea, *Houttuynia cordata* tea, Puer tea, Mate tea, Rooibos tea, Gimunema tea, Guava tea, coffee, espresso, and hot and cold espresso and coffee products obtained by mixing espresso and/or coffee with milk, water or other liquids suitable for oral consumption (e.g., lattes, cafe au lait, cafe mocha) and cocoa; 5) soups such as Japanese flavor soup, western flavor soup, and Chinese flavor soup; 6) seasonings; 7) various instant beverages and foods; 8) various snack foods; and 9) other compositions for oral use.

As described herein, the compositions of this disclosure can be used in a broad range of fragrance and flavor applications, e.g., fine fragrances, household products, laundry products, personal care products and cosmetics. The flavor use can be in foodstuffs such as soups, beverages, dairy products, confectionaries, cereals, snack, etc. These compositions can be employed in widely varying amounts, depending upon the specific application and on the nature and amounts of other odor or taste carrying ingredients. But because of the exceptional strength of these compositions, the effect can be achieved at a very low level of incorporation.

Preferred embodiments of this disclosure are described in the clauses below.

1. A composition comprising: (i) at least one material having odor strength or olfactive character; and (ii) at least one fenchol, wherein the at least one fenchol is selected from the group consisting of an alkylated fenchol, an isomeric, diastereomeric or enantiomeric alkylated fenchol, or mixtures thereof, and wherein the at least one fenchol is present in an amount effective to enhance odor strength or olfactive character of the composition.

2. The composition of clause 1 wherein the at least one material having odor strength or olfactive character is selected from the group consisting of a natural oil, a bio-based material, a synthetic material, a flavor material, and a fragrance material.

3. The composition of clause 1 wherein the at least one material having odor strength or olfactive character is selected from the group consisting of an essential oil, a single or compounded synthetic material, a flavor material, and a fragrance material.

4. The composition of clause 1 wherein the at least one fenchol is represented by the formula

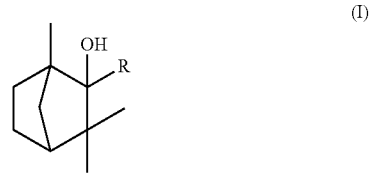

(I)

wherein R is a substituted or unsubstituted, branched or straight chain, alkyl or alkene group having from 1 to about 20 carbon atoms; and isomers, diastereomers and enantiomers of the fenchols of structure (I).

5. The composition of clause 4 wherein R is methyl, ethyl, propyl, butyl, tert-butyl, pentyl, hexyl, heptyl, octyl, nonyl, decyl, undecyl, dodecyl, allyl or vinyl.

6. The composition of clause 1 wherein the at least one fenchol is at least one C1-C12 alkylated fenchol or mixtures thereof, or at least one C1-C12 isomeric, diastereomeric or enantiomeric alkylated fenchol or mixtures thereof, or a mixture of at least one C1-C12 alkylated fenchol and at least one C1-C12 isomeric, diastereomeric or enantiomeric alkylated fenchol.

7. The composition of clause 1 wherein the at least one fenchol is present in an amount of from about 0.1 ppb to about 1000 ppm by weight, based on the total weight of the composition, to enhance odor strength or olfactive character of the composition.

8. The composition of clause 1 wherein the at least one fenchol is present in an amount of from about 0.1 ppb to about 500 ppm by weight, based on the total weight of the composition, to enhance odor strength or olfactive character of the composition.

9. The composition of clause 1 wherein the at least one fenchol is present in an amount of at least about 1 ppm by weight, based on the total weight of the composition, to enhance odor strength or olfactive character of the composition.

10. A synergistic composition comprising: (i) at least one material having odor strength or olfactive character; and (ii) at least one fenchol, wherein the at least one fenchol is selected from the group consisting of an alkylated fenchol, an isomeric, diastereomeric or enantiomeric alkylated fenchol, or mixtures thereof, wherein the at least one fenchol is present in an amount effective to enhance odor strength or olfactive character of the composition; and wherein the synergistic combination of the at least one material having odor strength or olfactive character and the at least one fenchol produces a combined effect greater than the sum of their separate effects for odor strength or olfactive character.

11. The synergistic composition of clause 10 wherein the at least one material having odor strength or olfactive character is selected from the group consisting of a natural oil, a bio-based material, a synthetic material, a flavor material, and a fragrance material.

12. The synergistic composition of clause 10 wherein the at least one material having odor strength or olfactive character is selected from the group consisting of an essential oil, a single or compounded synthetic material, a flavor material, and a fragrance material.

13. The synergistic composition of clause 10 wherein the at least one fenchol is represented by the formula

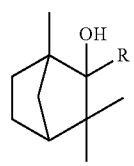

(I)

wherein R is a substituted or unsubstituted, branched or straight chain, alkyl or alkene group having from 1 to about 20 carbon atoms; and isomers, diastereomers and enantiomers of the fenchols of structure (I).

14. The synergistic composition of clause 13 wherein R is methyl, ethyl, propyl, butyl, tert-butyl, pentyl, hexyl, heptyl, octyl, nonyl, decyl, undecyl, dodecyl, allyl or vinyl.

15. The synergistic composition of clause 10 wherein the at least one fenchol is at least one C1-C12 alkylated fenchol or mixtures thereof, or at least one C1-C12 isomeric, diastereomeric or enantiomeric alkylated fenchol or mixtures thereof, or a mixture of at least one C1-C12 alkylated fenchol and at least one C1-C12 isomeric, diastereomeric or enantiomeric alkylated fenchol.

16. The synergistic composition of clause 10 wherein the at least one fenchol is present in an amount of from about 0.1 ppb to about 1000 ppm by weight, based on the total weight of the composition, to enhance odor strength or olfactive character of the composition.

17. The synergistic composition of clause 10 wherein the at least one fenchol is present in an amount of from about 0.1 ppb to about 500 ppm by weight, based on the total weight of the composition, to enhance odor strength or olfactive character of the composition.

18. The synergistic composition of clause 10 wherein the at least one fenchol is present in an amount of at least about 1 ppm by weight, based on the total weight of the composition, to enhance odor strength or olfactive character of the composition.

19. A consumer product containing the composition of clause 1.

20. The consumer product of clause 19 selected from the group consisting of a candle, an air care product, a perfume, a cologne, a soap, a personal care product, a detergent, a fabric care product, and a household cleaning product.

21. The consumer product of clause 19 selected from the group consisting of a soap, a detergent, an air freshener, a room spray, a pomander, a candle, and a cosmetic comprising a cream, an ointment, a toilet water, a pre-shave lotion, an aftershave lotion, a talcum powder, a hair-care agent, a body deodorant, and an anti-perspirant.

22. The consumer product of clause 19 selected from the group consisting of an air care product, a perfume, and a cologne.

23. The consumer product of clause 19 selected from the group consisting of a beverage, a powder or semi-frozen/frozen concentrate for a drink, a candy, a sugarless candy, a chocolate, a chewing gum, a bubble gum, a condiment, a spice, a seasoning, a dry cereal, an oatmeal, a granola bar, an alcoholic beverage, an energy beverage, a juice, a tea, a coffee, a salsa, a gel bead, a film strip for halitosis, a lozenge, a cough drop, a throat lozenge, a throat spray, a toothpaste, and a mouth rinse.

24. The consumer product of clause 19 selected from the group consisting of a beverage, a dairy product, a confectionary, a cereal, a snack, and a soup.

25. The consumer product of clause 19 selected from the group consisting of a beverage, a chewing gum, and a bubble gum.

26. A method of enhancing odor strength or olfactive character of a composition, said composition comprising: (i) at least one material having odor strength or olfactive character; and (ii) at least one fenchol, wherein the at least one fenchol is selected from the group consisting of an alkylated fenchol, an isomeric, diastereomeric or enantiomeric alkylated fenchol, or mixtures thereof, wherein said method comprises adding the at least one fenchol to the at least one material having odor strength or olfactive character in an amount effective to enhance odor strength or olfactive character of the composition.

27. The method of clause 26 comprising adding the at least one fenchol to the at least one material having odor strength or olfactive character in an amount effective to synergistically enhance odor strength or olfactive character of the composition.

28. The method of clause 26 wherein the at least one material having odor strength or olfactive character is selected from the group consisting of a natural oil, a bio-based material, a synthetic material, a flavor material, and a fragrance material.

29. The method of clause 26 wherein the at least one material having odor strength or olfactive character is selected from the group consisting of an essential oil, a single or compounded synthetic material, a flavor material, and a fragrance material.

30. The method of clause 26 wherein the at least one fenchol is represented by the formula

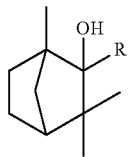

wherein R is a substituted or unsubstituted, branched or straight chain, alkyl or alkene group having from 1 to about 20 carbon atoms; and isomers, diastereomers and enantiomers of the fenchols of structure (I).

31. The method of clause 30 wherein R is methyl, ethyl, propyl, butyl, tert-butyl, pentyl, hexyl, heptyl, octyl, nonyl, decyl, undecyl, dodecyl, allyl or vinyl.

32. The method of clause 26 wherein the at least one fenchol is at least one C1-C12 alkylated fenchol or mixtures thereof, or at least one C1-C12 isomeric, diastereomeric or enantiomeric alkylated fenchol or mixtures thereof, or a mixture of at least one C1-C12 alkylated fenchol and at least one C1-C12 isomeric, diastereomeric or enantiomeric alkylated fenchol.

33. The method of clause 26 wherein the at least one fenchol is present in an amount of from about 0.1 ppb to about 1000 ppm by weight, based on the total weight of the composition, to enhance odor strength or olfactive character of the composition.

34. The method of clause 26 wherein the at least one fenchol is present in an amount of from about 0.1 ppb to about 500 ppm by weight, based on the total weight of the composition, to enhance odor strength or olfactive character of the composition.

35. The method of clause 26 wherein the at least one fenchol is present in an amount of at least about 1 ppm by weight, based on the total weight of the composition, to enhance odor strength or olfactive character of the composition.

While we have shown and described several embodiments in accordance with our disclosure, it is to be clearly understood that the same may be susceptible to numerous changes apparent to one skilled in the art. Therefore, we do not wish to be limited to the details shown and described but intend to show all changes and modifications that come within the scope of the appended claims.

The following examples are only to illustrate the preparation and use of the fenchols according to the disclosure. The disclosure is not limited thereto.

EXAMPLES

Evaluation of Materials Having Odor Strength or Olfactive Character with and without Fenchols Blotters were prepared for materials having odor strength or olfactive character (e.g., rosemary essential oil, nutmeg essential oil, Clearwood bio-based material, Patchouli essential oil and a natural/synthetic mixture) with or without fenchols (e.g., fenchol, methyl fenchol and 2-ethyl fenchol) as shown in FIG. 1. A double blind panel was assembled where the panelists were asked to select only the strongest blotter for each material tested. The responses are based on the trained expertise of the panelists, where each number represents the number of panelists that chose that blotter for that particular material. The results are shown in FIG. 1.

Preparation of Compounded Fragrance

A compounded fragrance was prepared having the following formula. Terrasol is ethyl fenchol.

| | |
|---|---|
| Gamma Nonalactone | .5 |
| Isobutyl Quinoline | 1.0 |
| Black Pepper EO | 10.0 |
| Clary Sage EO | 10.0 |
| Allspice EO | 16.0 |
| Nutmeg EO | 17.5 |
| Iso E Super | 30.0 |
| Terrasol @ 0.1% | 1.0 |
| Dipropylene Glycol | 14.0 |
| Total | 100.0 |

Preparation of Compounded Flavor

A compounded flavor was prepared having the following formula. Terrasol is ethyl fenchol.

| | |
|---|---|
| 1.00¤ | 6-METHYL•COUMARIN¤ |
| 0.15¤ | ACETOIN¤ |
| 10.00¤ | ALDEHYDE-C-18•(GAMMA•NONALACTONE)¤ |
| 1.00¤ | BENZALDEHYDE¤ |
| 1.00¤ | BENZODIHYDRO•PYRONE¤ |
| 15.00¤ | BENZLY•ALCOHOL¤ |
| 5.00¤ | CITRAL•NAT¤ |
| 1.00¤ | CYCLOTENE¤ |
| 1.00¤ | ETHYL•BUTYRATE¤ |
| 0.50¤ | GAMMA•HEXALACTONE¤ |
| 0.25¤ | GAMMA•OCTALACTONE¤ |
| 5.00¤ | LIME•OIL•DISTILLED•W.I.¤ |
| 17.50¤ | LIME•OIL•EXPRESSED¤ |
| 10.00¤ | LIME•TERPENES¤ |
| 0.50¤ | MALTOL¤ |
| 2.50¤ | ORANGE•OIL•FLORIDA¤ |
| 10.00¤ | ORANGE•TERPENES¤ |
| 6.75¤ | VANILLIN¤ |
| 0.50¤ | Terrasol•(1%-MCT)¤ |
| 11.35¤ | MCT¤ |

A compounded spice market fragrance was prepared having the following formula. Terrasol is ethyl fenchol.

| Spice Market | |
|---|---|
| Product Name | Parts |
| Gamma Nonalatone | 5 |

-continued

Spice Market

| Product Name | Parts |
|---|---|
| Isobutyl Quinoline | 10 |
| Black Pepper essential oil | 100 |
| Clary Sage essential oil | 100 |
| Allspice essential oil | 160 |
| Nutmeg essential oil | 175 |
| Iso E Super | 300 |
| DPG (solvent) | 149 |
| Terrasol @ 0.01% DPG | 1 |
| Total | 1000 |

Spice market fragrance materials are prepared with or without fenchols as shown in FIG. 2. A double blind panel is assembled where the panelists are asked to select only the strongest spice market fragrance for each material tested. The responses are based on the trained expertise of the panelists, where each number represents the number of panelists that chose that particular fragrance. The panelists are presented with the spice market fragrance and determine which they feel is stronger in a comparison of fragrance without fenchols versus fragrance with various fenchols. The results are shown in FIG. 2.

Compounded flavors (i.e., key lime coconut, mouthwash and tequila) are prepared having the following formulas.

KEY LIME COCONUT FLAVOR

| A | B | |
|---|---|---|
| 2.50 | 2.50 | ORANGE OIL FLORIDA |
| 5.00 | 5.00 | CITRAL NAT |
| 5.00 | 5.00 | LIME OIL DISTILLED |
| 10.00 | 10.00 | ORANGE TERPENES |
| 10.00 | 10.00 | LIME TERPENES |
| 17.50 | 17.50 | LIME OIL EXPRESSED |
| 50.00 | 50.00 | COCONUT FLAVOR |
|  | 0.50 | 2-ETHYL FENCHOL 1% (MCT*) |
| 100.00 | 100.50 | |

*Medium Chained Triglycerides
USE LEVEL IN WHITE CHOCOLATE CANDY = 0.25%
ETHYL FENCHOL LEVELS
0.005%/50 PPM IN FLAVOR
0.125 PPM IN FINISHED CANDY
RESULTS:
ETHYL FENCHOL BOOSTS THE FRESH LIME JUICE CHARACTER IN THE FINISHED PRODUCT AND IS PREFERRED.

MOUTHWASH FLAVOR

| A | B | |
|---|---|---|
| 3.00 | 3.00 | MENTHOL CRYSTALS |
| 0.10 | 0.10 | EUCALYPTOL |
| 3.00 | 3.00 | PEPPERMINT OIL REDISTILLED |
| 4.00 | 4.00 | METHYL SALICYLATE |
| 3.50 | 3.50 | EUGENOL |
| 86.40 | 86.39 | PROPYLENE GLYCOL |
|  | 0.01 | 2-ETHYL FENCHOL (1% IN ETHANOL) |
| 100.00 | 100.00 | |

USE LEVEL IN ETHANOL-FREE MOUNTWASH BASE = 0.5%
BEDOUKAIN RESEARCH
FENCHOLS PATENT ATTACHMENTS
5 PPT (PARTS PER TRILLION) IN MOUTHWASH
RESULTS:

MOUTHWASH FLAVOR

| A | B |
|---|---|

2-ETHYL FENCHOL BOOSTS THE MENTHOL COOLING NOTES WHILE ADDING A MEDICINAL, ANTISEPTIC CHARACTER TYPICAL OF LEADING BRAND MOUTHWASHES.

TEQUILA FLAVOR

| A | B | |
|---|---|---|
| 8.00 | 8.00 | ISOAMYL ALCOHOL |
| 1.60 | 1.60 | ISOBUTYL ALCOHOL |
| 0.40 | 0.40 | DIETHYL ACETAL |
| 8.00 | 8.00 | RUM ETHER |
| 20.00 | 20.00 | BROWN SUGAR EXTRACT |
| 0.40 | 0.40 | COGNAC OIL REPLACER |
| 20.00 | 20.00 | ETHYL ALCOHOL |
| 40.80 | 40.70 | PROPYLENE GLYCOL |
| 0.80 | 0.80 | WINE FUSEL OIL |
| 0.00 | 0.10 | FENCHOL ALCOHOL 10% IN ETHYL ALCOHOL |
| 100.00 | 100.00 | |
| 8.00 | 8.00 | ISOAMYL ALCOHOL |
| 1.60 | 1.60 | ISOBUTYL ALCOHOL |
| 0.40 | 0.40 | DIETHYL ACETAL |
| 8.00 | 8.00 | RUM ETHER |
| 20.00 | 20.00 | BROWN SUGAR EXTRACT |
| 0.40 | 0.40 | COGNAC OIL REPLACER |
| 20.00 | 20.00 | ETHYL ALCOHOL |
| 40.80 | 40.70 | PROPYLENE GLYCOL |
| 0.80 | 0.80 | WINE FUSEL OIL |
| 0.00 | 0.10 | FENCHOL ALCOHOL 10% IN ETHYL ALCOHOL |
| 100.00 | 100.00 | |

USE LEVEL 0.5% IN ALCOHOLIC BEVERAGE
FENCHYL ALCOHOL 0.01% (100 PPM) IN FLAVOR
0.5 PPM IN FINISHED BEVERAGE
RESULTS:
FENCHOL ADDS EARTHY, MUSTY NOTES FOUND IN TOP SHELF TEQUILA

Key lime coconut, mouthwash and tequila flavor materials are prepared with or without fenchols as shown in FIG. 3. A double blind panel is assembled where the panelists are asked to select only the strongest key lime coconut, mouthwash and tequila flavor for each material tested. The responses are based on the trained expertise of the panelists, where each number represents the number of panelists that chose that particular fragrance. The panelists are presented with the key lime coconut, mouthwash and tequila flavor and determine which they feel is stronger in a comparison of flavor without fenchols versus flavor with various fenchols. The results are shown in FIG. 3.

Various essential oil fragrance materials were prepared with or without ethyl fenchol as shown in FIG. 4. A double blind panel was assembled where the panelists were asked to select only the strongest essential oil fragrance for each material tested. The responses were based on the trained expertise of the panelists, where each number represents the number of panelists that chose that particular essential oil fragrance. The panelists were presented with the essential oil fragrance and determined which they felt was stronger in a comparison of essential oil fragrance without ethyl fenchol versus essential oil fragrance with ethyl fenchol. The results are shown in FIG. 4.

Professional flavorists and perfumers were presented with the key lime coconut flavor with Terasol (i.e., ethyl fenchol) described above and the spice market fragrance with Terasol described above, respectively. The professional flavorists and perfumers were then asked to comment the flavor and fragrance. The comments are summarized below.

Key Lime Coconut Flavor

Flavorist 1: definitely enhances coconut note . . . like the lemon/lime aspect to it . . . would work in cola flavors;
Flavorist 2: brought out the lime and lowered the coconut . . . rounds out the flavor;
Flavorist 3: really like the effect . . . more like real fruit now . . . boosts the lime . . . really nice one;
Flavorist 4: the lime is really strong . . . brings out the juiciness of the lime;
Flavorist 5: flavor becomes sparkly . . . quite unique material;
Flavorist 6: fuller and more creamy . . . more true to the key lime pie;
Flavorist 7: enhanced the lime a lot . . . actually amazing, the lime flavor is much more natural . . . really delicious . . . really good the longer you keep it in your mouth . . . the lime became more of a fresh squeezed lime . . . adds juicy notes which can be rather difficult in a chocolate;
Flavorist 8: makes the lime really pop . . . very nice;
Flavorist 9: was not expecting that type of effect . . . makes it go from something terpenic to a real juicy, naturalness type of flavor . . . really good and really interesting;
Flavorist 10: lime note comes up stronger . . . the effect is there from the ingredient;
Flavorist 11: really increased the lime notes and turns more characteristic enhancing the skin notes of the lime . . . lime profile becomes well defined . . . offers more of a lime peely effect and makes the coconut softer, but blends together nicely . . . turns it from a candy/artificial coconut flavor to more of a natural flavor;
Flavorist 12: more terpenic notes . . . very interesting profile . . . more of a really green lime . . . enhances the lime.

Spice Market Fragrance

Perfumer 1: much more body . . . a nice earthy, camphoraceous effect;
Perfumer 2: brings the freshly crushed nutmeg to light . . . smells more natural and true to life;
Perfumer 3: pushes the nutmeg big time
Perfumer 4: boosts spice notes . . . makes the nutmeg bloom more . . . effect is incredible, especially given the dose level . . . impressive;
Perfumer 5: wraps up the spice notes well . . . very interesting effect;
Perfumer 6: this is interesting . . . very nice . . . an unbelievable effect.
Perfumer 7: effects are impressive;
Perfumer 8: interesting . . . very nice effect;
Perfumer 9: makes everything brighter in the fragrance . . . has a huge effect.

The present disclosure is not to be limited in scope by the specific embodiments described herein. Indeed, various modifications of the disclosure in addition to those described herein will become apparent to those skilled in the art from the foregoing description. Such modifications are intended to fall within the scope of the appended claims.

What is claimed is:

1. A composition consisting essentially of: (i) at least one fragrance material having odor strength or olfactive character; and (ii) at least one fenchol, wherein the at least one fenchol is selected from the group consisting of an alkylated fenchol, an isomeric, diastereomeric or enantiomeric alkylated fenchol, and mixtures thereof; and wherein the at least one fenchol is present in an amount effective to enhance odor strength or olfactive character of the at least one fragrance material;
wherein the at least one fragrance material is selected from the group consisting of essential oils, essential oils of synthetic origin, essential oils of natural origin, and combinations thereof; and
wherein the at least one fenchol is represented by the formula

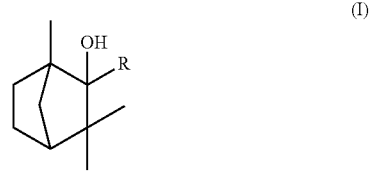

wherein R is a substituted or unsubstituted, branched or straight chain, alkyl or alkene group having from 1 to about 20 carbon atoms; and isomers, diastereomers and enantiomers of the fenchols of structure (I).

2. The composition of claim 1 wherein R is methyl, ethyl, propyl, butyl, tert-butyl, pentyl, hexyl, heptyl, octyl, nonyl, decyl, undecyl, dodecyl, allyl or vinyl.

3. The composition of claim 1 wherein the at least one fenchol is present in an amount of from about 0.1 ppb to about 1000 ppm by weight, based on the total weight of the composition, to enhance odor strength or olfactive character of the at least one material.

4. The composition of claim 1 wherein the at least one fenchol is present in an amount of from about 0.1 ppb to about 500 ppm by weight, based on the total weight of the composition, to enhance odor strength or olfactive character of the at least one material.

5. The composition of claim 1 wherein the at least one fenchol is present in an amount of at least about 1 ppm by weight, based on the total weight of the composition, to enhance odor strength or olfactive character of the at least one material.

6. A consumer product containing the composition of claim 1.

7. The consumer product of claim 6 selected from the group consisting of a candle, an air care product, a perfume, a cologne, a soap, a personal care product, a detergent, a fabric care product, and a household cleaning product.

8. The consumer product of claim 6 selected from the group consisting of a soap, a detergent, an air freshener, a room spray, a pomander, a candle, and a cosmetic comprising a cream, an ointment, a toilet water, a pre-shave lotion, an aftershave lotion, a talcum powder, a hair-care agent, a body deodorant, and an anti-perspirant.

9. The consumer product of claim 6 selected from the group consisting of an air care product, a perfume, and a cologne.

10. The composition of claim 1, wherein the at least one fragrance material is selected from the group consisting of rosemary essential oil, nutmeg essential oil, Patchouli essential oil, cardamom essential oil, cinnamon leaf essential oil, clove leaf essential oil, elemi essential oil, sandalwood essential oil, rose essential oil, clearwood essential oil, cashmeran essential oil, lemon essential oil, ginger essential oil, black pepper essential oil, clary sage essential oil, allspice essential oil, and combinations thereof.

11. The composition of claim 1, wherein the at least one fragrance material comprises at least one essential oil.

12. A method of enhancing odor strength or olfactive character of a composition, said composition consisting essentially of: (i) at least one fragrance material having odor strength or olfactive character; and (ii) at least one fenchol, wherein the at least one fenchol is selected from the group consisting of an alkylated fenchol, an isomeric, diastereomeric or enantiomeric alkylated fenchol, or mixtures thereof; wherein said method comprises adding the at least one fenchol to the at least one fragrance material in an amount effective to enhance odor strength or olfactive character of the at least one fragrance material;
wherein the at least one fragrance material is selected from the group consisting of essential oils, essential oils of synthetic origin, essential oils of natural origin, and combinations thereof; and
wherein the at least one fenchol is represented by the formula

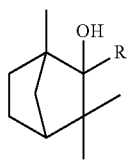

(I)

wherein R is a substituted or unsubstituted, branched or straight chain, alkyl or alkene group having from 1 to about 20 carbon atoms; and isomers, diastereomers and enantiomers of the fenchols of structure (I).

13. The method of claim 12, wherein the at least one fragrance material is selected from the group consisting of rosemary essential oil, nutmeg essential oil, Patchouli essential oil, cardamom essential oil, cinnamon leaf essential oil, clove leaf essential oil, elemi essential oil, sandalwood essential oil, rose essential oil, clearwood essential oil, cashmeran essential oil, lemon essential oil, ginger essential oil, black pepper essential oil, clary sage essential oil, allspice essential oil, and combinations thereof.

14. The method of claim 12, wherein the at least one fragrance material comprises at least one essential oil.

* * * * *